(12) United States Patent
Roitman et al.

(10) Patent No.: US 7,846,396 B2
(45) Date of Patent: Dec. 7, 2010

(54) SAMPLE HOLDER FOR SURFACE PLASMON RESONANCE MEASURING INSTRUMENTS

(75) Inventors: Daniel B. Roitman, Menlo Park, CA (US); Gregory D. VanWiggeren, San Jose, CA (US)

(73) Assignee: Sierra Sensors GmbH, Hamburg (DE)

( * ) Notice: Subject to any disclaimer, the term of this patent is extended or adjusted under 35 U.S.C. 154(b) by 948 days.

(21) Appl. No.: 11/141,167

(22) Filed: May 31, 2005

(65) Prior Publication Data

US 2006/0269453 A1    Nov. 30, 2006

(51) Int. Cl.
*B01L 3/00* (2006.01)
(52) U.S. Cl. .............. 422/102; 422/82.05; 422/82.11; 422/104; 436/86; 436/173; 436/174; 250/281; 250/288; 356/445
(58) Field of Classification Search .............. 422/82.05, 422/102, 82.11, 104; 436/86, 173, 174; 250/281; 250/288; 356/445
See application file for complete search history.

(56) References Cited

U.S. PATENT DOCUMENTS 6,514,702 B1 * 2/2003 Okano et al. ................ 435/6
2003/0052002 A1 * 3/2003 Vogel et al. ............ 204/403.01

OTHER PUBLICATIONS

Suzuki et al, "Evaporative Concentration of Analytes and Sensing Using a Super Hydrophobic Surface", Oct. 24, 2004, IEEE, pp. 712-715.*

* cited by examiner

*Primary Examiner*—Jill Warden
*Assistant Examiner*—Dennis M White
(74) *Attorney, Agent, or Firm*—Boyle Fredrickson S.C.

(57) ABSTRACT

A droplet sample holder, especially a sample holder for use in a measuring instrument utilizing surface plasmon resonance. The sample holder reduces or minimizes the measurement distortion result of the droplet "pherpheral concentration effect" by surrounding the analysis zone with a wettable (hydrophilic) zone that captures the periphery of the droplet to keep the pheriphery of the droplet and the increased concentration of the analyte out of the analysis zone. The wettable zone is surrounded by a nonwettable (hydrophobic) zone that restricts the periphery of the droplet to analysis zone and the wettable zone.

14 Claims, 2 Drawing Sheets

SAMPLE HOLDER FOR SURFACE PLASMON RESONANCE MEASURING INSTRUMENTS

STATEMENT REGARDING FEDERALLY SPONSORED RESEARCH OR DEVELOPMENT

This invention has been created without the sponsorship or funding of any federally sponsored research or development program.

BACKGROUND OF THE INVENTION

This present invention relates generally to sample holders for measuring instruments and specifically to sample holders for instruments which utilize surface plasmon resonance (SPR) for measuring chemical or biochemical compositions. Surface plasmon resonance is being used in biosensing, in such areas as immunoassay and nucleic acid detection Basically, surface plasmons are electromagnetic waves created along an interface between a conducting material and a non-conducting material. A common technique for their creation is to direct a beam of electromagnetic radiation into a glass prism with an angle of incidence above the critical angle so that it undergoes total internal reflection. The internal reflection creates an evanescent electromagnetic wave at a region outside of the prism adjacent to the surface. When a thin conductive film is deposited on the surface of the prism, surface plasmons will be formed.

Surface plasmon resonance occurs when the momentum (or the wave vector) and energy (i.e. frequency) of the evanescent electromagnetic wave are made to match the momentum and energy of the surface plasmons respectively. It is characterized by a sharp decrease in intensity of the reflected beam as its energy is transferred, because of the resonance, to the surface plasmons.

The wave vector $K_e$ of the evanescent wave is defined by the equation:

$$K_e = (\omega/C) n \sin \Theta,$$

where $\omega$ is the angular frequency of the incident beam, c is the speed of light in vacuum, n is the refractive index of glass and $\Theta$ is the angle of incidence. The wave vector of the surface plasmon is defined by the equation:

$$K_{sp} = (\omega/c)(1/\epsilon_m + 1/\epsilon_s) - \frac{1}{2},$$

where $\epsilon_m$ is the real part of the dielectric constant of the metal and $\epsilon_s$ is the dielectric constant of the substance under test (or in the absence of any substance, of air) surrounding the metal.

At resonance, the wave vector of the evanescent wave is the same as that of the surface plasmons so that there is no electromagnetic wave reflected from the surface. Therefore, occurrence of the surface plasmon resonance is given by the equation:

$$K_e = K_{sp}.$$

If a periodic structure such as a grating or a surface acoustic wave is impressed upon the thin metal layer, the above equation becomes:

$$K_e + k = K_{sp}.$$

where k is the wave vector due to the periodic structure.

The above equation provides a useful tool for measuring differences between the values of $\epsilon_s$ of different materials. It also provides a useful tool for detecting the presence of trace surface chemicals in a substance that alters its $\epsilon_s$ value. By measuring the differences of $K_e$ at resonance, the changes in $\epsilon_s$ can be determined.

Surface plasmon resonance measuring instruments typically utilize the above equality condition and measure the differences of $K_e$ by varying $\Theta$ and sensing the reflected beam at different values of $\Theta$ to detect the resonance. In these surface plasmon resonance measuring instruments, sensing the reflected beam at different values of $\Theta$ has been accomplished by various methods. Other surface plasmon resonance measuring instruments utilize the above equality condition and measure the differences of $K_e$ by varying parameters and sensing the reflected beam at different values of the varied parameter.

In the typical surface plasmon resonance measuring instrument, the sample to be measured are placed in a pattern of droplets on a gold surface of a glass slide. The gold coated slide is referred to as a chip.

The present invention is directed generally to surface Plasmon Resonance technology (SPR) which allows the characterization of bio specific interactions of label-free compounds. The invention is specifically directed to a variation of SPR known as the Kretchmann process and, more specifically, to the substrate or chip that is part of the process. In the Kretchmann process, a collimated beam of light, e.g. laser, is directed through a prism to a chip that is supported on the prism. The chip is glass slide coated with metal such as silver or gold. The light hits the glass gold interface. At a specific angle, the light will be absorbed. The nonabsorbed light is reflected back through the prism and detected. Biological samples to be analyzed are deposited on the gold in an array of droplets. Each droplet has a target biological element bound to a ligand, for example, that will have an effect on the reflected light to the detector which will be indicative of the specific biological element in the droplet.

More specifically, the Kretchman process uses a constant wave-length light source, e.g. laser. The laser light is directed through a P-polarizer to pass only the P-polarized light. The light is then directed through a prism. A glass slide coated with gold is positioned fixed on the hypotenuse of the prism with refractive index matching fluid. The light hits the glass gold interface. At a specific angle, the light will be absorbed. The non-absorbed light is reflected and detected using a photomultiplier tube or CCD camera.

One of the problems associated with conventional chips is that as the droplet spreads over the gold surface and as the droplet dries, the analyte migrates to the periphery of the droplet, so that there is a higher concentration of biological material at the periphery of the droplet than in the body of the droplet. This non-uniform distribution of analyte in the droplet, or "peripheral concentration effect", can produce a distortion of the light signal received by the detector, and interferes with the ability of the device to correctly analyze the content of the droplet.

What is needed is a sample holder for an instrument that can be used for measuring chemical compositions by measuring the dielectric constants thereof utilizing surface plasmon resonance, said sample holder being designed so that the measurement distorting result of the sample droplet "peripheral concentration effect" is minimized or eliminated.

SUMMARY OF THE INVENTION

This invention is directed to a droplet sample holder, and especially a droplet sample holder surface for use in a plasmon resonance (SPR) measuring instrument.

In one implementation, the measuring instrument comprises a block of material transparent to a beam of electromagnetic radiation. This block of material has a surface for providing internal reflection of an electromagnetic radiation beam and one or more separate electrically conductive spots on the outside of the surface. The instrument has a source projecting a source beam of electromagnetic radiation onto a beam steering device. The beam steering device receives the source beam and transmits it into the block at an adjustable angle of incidence to a reflection point on the block surface. In the case of a single spot, the spot is located at the reflection point. In the case of the plurality of spots, a translation system is provided so that each of the spots can be selectively located at the reflecting point. Detection of the reflected beam from each spot is performed through a detector.

The "peripheral concentration effect" problem found in the prior art is overcome by the chip of the present invention in which the continuous coating of gold of the prior art chips is replaced by one or an array of separate electrically conductive spots. The chip of the present invention comprises a glass slide that carries one or an array of separate electrically conductive spots. Each spot can be of any shape, but is preferably round. Each spot is surrounded by a layer of wettable (hydrophilic) material which is, in turn, surrounded by a layer of nonwettable (hydrophobic) material. The wettable layer attracts the periphery of the droplet on the surrounded spot and insures that the edges of the droplet are outside of surrounded spot. This moves the droplet periphery, in which periphery the analyte is concentrated, off the spot, and leaves only the central portion of the droplet, in which the analyte is uniformly concentrated, over the spot. This insures that the distribution of the analyte will be uniform across the spot and across the field of analysis. The nonwettable layer restricts the expansion of the droplet and keeps the droplet across the spot and the wettable layer.

It will be understood that the concept of wettable and nonwettable is relative to the composition of the droplet. In the typical case where the droplet is mainly water, the wettable means hydrophilic and nonwettable means hydrophobic. It should be understood, however, that the wettability or nonwettability of a surface is a function of the entire content of the droplet. Thus, the wettability or nonwettability of a surface to an aqueous droplet can be greatly affected if the droplet contains even small amounts of surface active molecules, such as detergents. More generally, the wettable surface has a surface energy higher than the surface energy of the droplet and the nonwettable surface has a surface energy lower than the surface energy of the droplet.

For a typical aqueous droplet, wettable surfaces include soda glass, and nonwettable surfaces include low-density polyethylene.

The chip is shown supported on the surface of a prism that forms part of the SPR apparatus. The apparatus also includes a source of light and a detector. The light source projects a beam of light through the prism to the electrically conductive spots. Light reflected from each spot is received and analyzed by the detector.

BRIEF DESCRIPTION OF THE DRAWINGS

The character of the invention, however, may best be understood by reference to one of its structural forms, as illustrated by the accompanying drawings, in which.

DESCRIPTION OF THE PREFERRED EMBODIMENT

Figure 1:
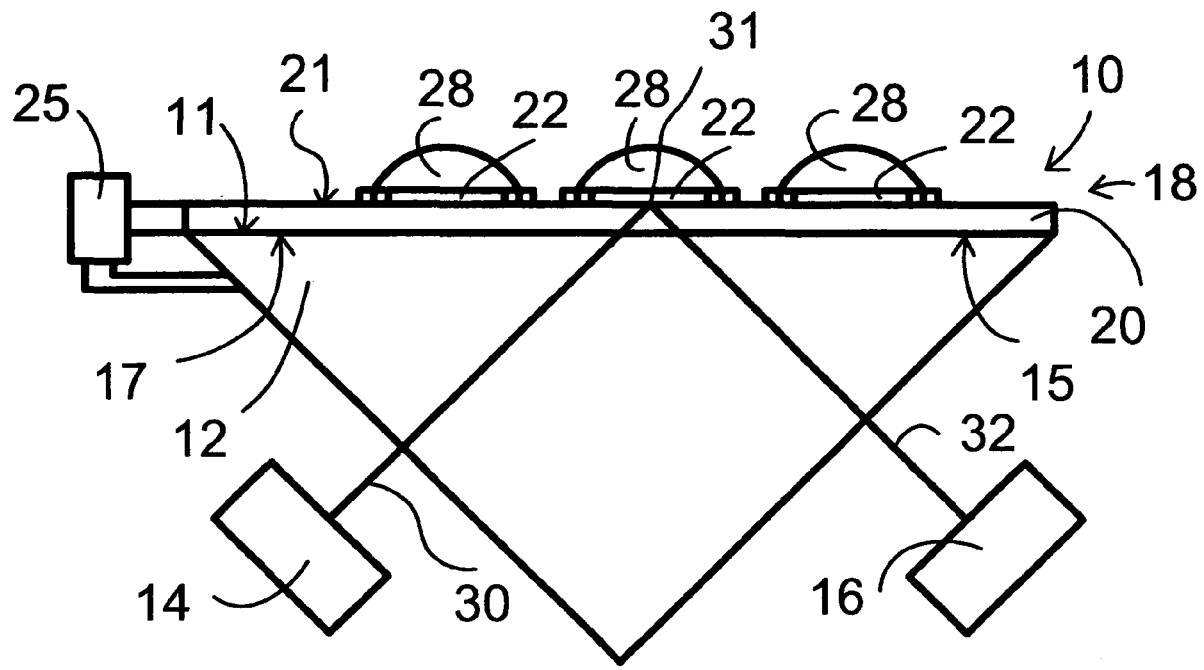
FIG. 1 is a diagrammatic front elevation view a surface plasmon resonance (SPR) measuring instrument and droplet holder embodying the principles of the present invention.

Referring first to FIG. 1 in which the general principles of the present invention are shown, the chip 18 is shown supported on and optically connected to the internally reflective surface 11 of a prism 12 that forms part of an SPR apparatus, generally indicated by the reference numeral 10. The chip 18 includes a glass slide 20, a plurality of electrically conductive spots 22 on the outside surface 21 of the glass slide 20, and, over each spot 22, the chip carries a droplet 28 to be analyzed. The apparatus 10 includes a source of light 14 and a detector 16. The light source 14 projects a beam of light 30 through the prism 12 to a reflective location 31 on the chip 18 and to an electrically conductive spot 22 on the chip 18 at that reflective location 31. Light reflected from the location 31 and spot 22, beam 32, is received and analyzed by the detector 16. A translation device 25 is provided to move the chip 18 relative to the prism 12 so that each of the spots 22 can be positioned at the reflective location 31 to reflect the beam 30. The space 15 between the prism 12 and the slide 20 is filed with an index matching fluid 17. The prism 12, the slide 20, and the fluid 17 all have the same index of refraction so that the space 15 causes no refraction of the beams 30 or 31.

Figure 2:
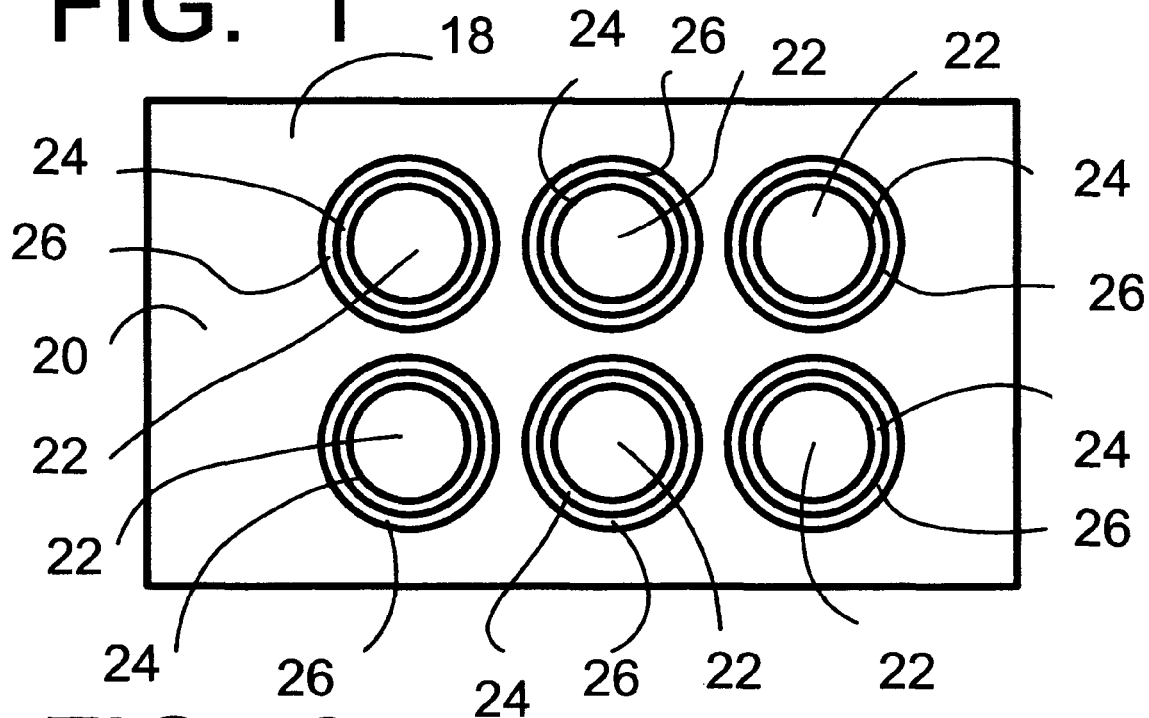
FIG. 2 is a plan view of a droplet holder embodying the principles of the present invention.

The "peripheral concentration effect" problem found in the prior art is overcome by the chip 18 of the present invention in which the continuous coating of gold of the prior art chips is replaced by one or an array of separate electrically conductive spots 22 as shown in a plan view in FIG. 2. The chip 18 comprises a glass slide 20 that carries one or an array of separate electrically conductive spots 22. Each spot 22 can be of any shape, but is preferably round. Each spot 22 is surrounded by a layer 24 of wettable (hydrophilic) material that is, in turn, surrounded by a layer 26 of nonwettable (hydrophobic) material. The wettable layer 24 attracts the periphery 29 of a droplet 28 (not shown) on the surrounded spot 22 and insures that the periphery 29 of the droplet 28 (not shown) is outside of surrounded spot 22. This moves the droplet periphery 29, in which periphery the analyte is concentrated, off the spot, and leaves only the central portion 27 of the droplet 28, in which the analyte is uniformly concentrated, over the spot 22. This insures that the distribution of the analyte will be uniform across the spot. The nonwettable layer 26 restricts the expansion of the droplet and keeps the droplet across the spot and the wettable layer 24.

Figure 3:
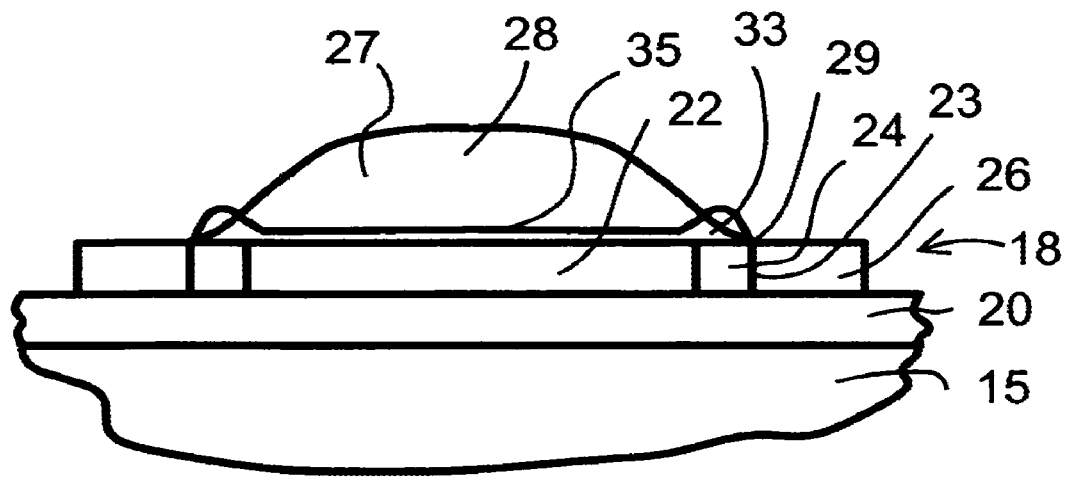
FIG. 3 is a close-up diagrammatic view of a small volume droplet on a droplet holder embodying the principles of the present invention.

FIG. 3 is a close-up front elevation view of a low volume droplet on the chip 18. The spot 22 on the slide 20 of the chip 18 is surrounded by a layer 24 of wettable (hydrophilic) material which is, in turn, surrounded by a layer 26 of nonwettable (hydrophobic) material. The wettable layer 24 attracts the periphery 29 of a droplet 28 on the surrounded spot 22, and draws the periphery of the droplet to the periphery of the wettable layer 23 and insures that the periphery 29 of the droplet 28 is outside of surrounded spot 22. This moves the droplet periphery 29, near which periphery the analyte is concentrated, off the spot, and leaves only the central portion 27 of the droplet 28, in which the analyte is uniformly concentrated, over the spot 28. This insures that the distribution of the analyte will be uniform across the spot. The periphery of the droplet will expand until it reaches the periphery 23 of the wettable layer and the boundary between the wettable and nonwettable layers, at which it will stop. The contact angle between wettable layer and the droplet surface will depend on the volume of the droplet. For low volume droplets, as represented by FIG. 3, the contact angle will be less than 90 degrees.

Line 35 is a diagrammatic representation of the concentration of the analyte across the diameter of the droplet 28. The height of the line 35 over the outer surface of the spot 22 and wettable layer 24 represents the concentration of the analyte in the droplet 28. The analyte is highly concentrated near the periphery 29 of the droplet and relatively lower and uniform over and across the spot 22 and the central portion 27 of the droplet 28. This uniformity of concentration over the spot 22 improves the effectiveness of the SPR apparatus 10. The nonwettable layer 26 restricts the expansion of the droplet and keeps the droplet across the spot and the wettable layer 24.

Figure 4:
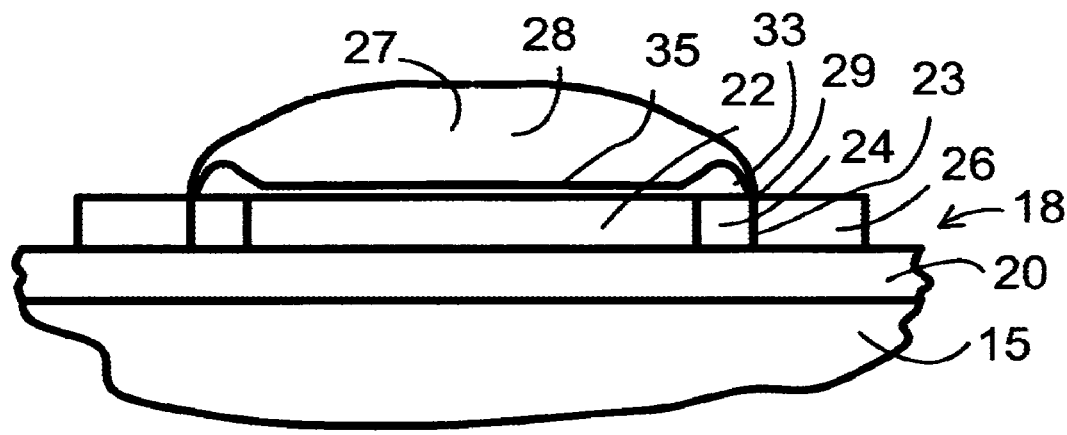
FIG. 4 is a close-up diagrammatic view of a medium volume droplet on a droplet holder embodying the principles of the present invention.

FIG. 4 shows the effect of increased volume in the droplet 28. As the volume increases, the contact angle 33 increases. FIG. 4 shows the contact angle at 90 degrees.

Figure 5:
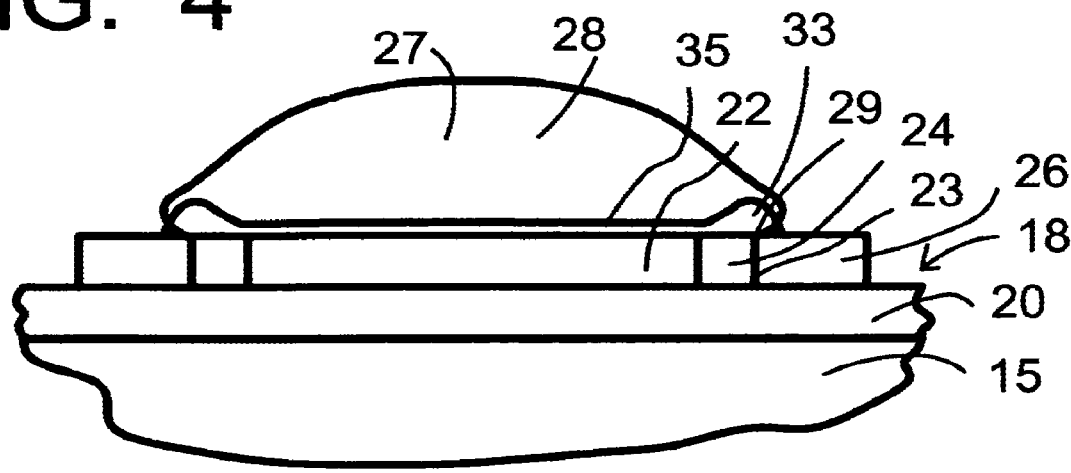
FIG. 5 is a close-up diagrammatic view of a high volume droplet on a droplet holder embodying the principles of the present invention.

FIG. 5 shows the effect of further increased volume in the droplet 28. As the volume increases, the contact angle 33 increases. FIG. 5 shows the contact angle at greater than 90 degrees.

After a droplet is analyzed, the translation device 25 moves a new stop 22 into the reflective location 31 so that the new spot 22 can be analyzed.

It will be understood that the concept of wettable and nonwettable is relative to the composition of the droplet. In the typical case where the droplet is mainly water, the wettable means hydrophilic and nonwettable means hydrophobic. It should be understood, however, that the wettability or nonwettability of a surface is a function of the entire content of the droplet. Thus, the wettability or nonwettability of a surface to an aqueous droplet can be greatly affected if the droplet contains even small amounts of surface-active molecules, such as detergents. More generally, the wettable surface has a surface energy or surface tension higher than the surface energy of the droplet and the nonwettable surface has a surface energy or surface tension lower than the surface energy of the droplet.

For a typical aqueous droplet, wettable surfaces include soda glass, and nonwettable surfaces include low-density polyethylene.

Although this invention is described with reference to specific parameters and implementations, it will be understood that various modifications can be made thereto without substantive departure from the scope of the invention, which is defined by the following claims.

We claim:

1. A droplet holder for holding a droplet, the holder comprising:
    a. a slide having a top and bottom surface,
    b. an electrically conductive spot on the top surface of the slide, the surface of the spot that is not in contact with the top surface of the slide exhibiting surface plasmon resonance when excited by light entering the bottom surface of the slide,
    c. a wettable zone on the top surface of the slide, the wettable zone being wettable by the droplet, and surrounding the conductive spot; and
    d. a nonwettable zone on the top surface of the slide, the nonwettable zone being nonwettable by the droplet, and surrounding the wettable zone.

2. A droplet holder as recited in claim 1, wherein the holder includes a plurality of separate conductive spots on the surface of the slide, and for each conductive spot, a wettable zone on the top surface of the slide surrounding that conductive spot, and, for each conductive spot, a nonwettable zone on the top surface of the slide surrounding the wettable zone.

3. A droplet holder as recited in claim 1, wherein the wettable zone captures the periphery of the droplet to keep the periphery of the droplet and the increased concentration of an analyte therein away from the conductive spot, leaving the relatively uniform concentration of the analyte in the central part of the droplet, the central part overlying the conductive spot to reduce the measurement distortion associated with the "peripheral concentration effect";
    and wherein the nonwettable zone restricts the periphery of the droplet to the wettable zone.

4. A droplet holder for holding a droplet having a surface energy, the droplet holder comprising:
    a. a slide having a top and bottom surface,
    b. an electrically conductive spot on the top surface of the slide, the surface of the spot that is not in contact with the top surface of the slide exhibiting surface plasmon resonance when excited by light entering the bottom surface of the slide,
    c. a wettable zone on the top surface of the slide, having a surface energy greater than the surface energy of the droplet, and surrounding the conductive spot; and
    d. a nonwettable zone on the top surface of the slide, the wettable zone having a surface energy less than the surface energy of the droplet, and surrounding the wettable zone.

5. A droplet holder as recited in claim 4, wherein the holder includes a plurality of separate conductive spots, and for each conductive spot, a wettable zone surrounds that conductive spot, and, for each conductive spot, a nonwettable zone surrounds the wettable zone.

6. A droplet holder as recited in claim 4, wherein the holder is adapted for use in a measuring instrument utilizing surface plasmon resonance to analyze an analyte in the droplet; and
    wherein the conductive spot has a first surface, having a first surface area, in contact with the top surface of the slide, and a second surface, having a second surface area equal to the first surface area, opposite to the first surface; and
    wherein the droplet covers the entire second surface area of the second surface of the conductive spot.

7. A droplet holder as recited in claim 4, wherein the wettable zone captures the periphery of the droplet to keep the periphery of the droplet and the increased concentration of the analyte therein away from the conductive spot, leaving the relatively uniform concentration of the analyte in the central part of the droplet, the central part overlying the conductive spot, to reduce the measurement distortion result of the droplet "peripheral concentration effect";
    and wherein the nonwettable zone restricts the periphery of the droplet to the wettable zone.

8. A droplet sample holder for holding an aqueous droplet, the sample holder comprising:
    a. a slide having a top and bottom surface,
    b. an electrically conductive spot on the top surface of the slide, the surface of the spot that is not in contact with the top surface of the slide exhibiting surface plasmon resonance when excited by light entering the bottom surface of the slide, c. a hydrophilic zone on the top surface of the slide surrounding the conductive spot, and
d. a hydrophobic zone on the top surface of the slide surrounding the hydrophilic zone.

9. A droplet holder as recited in claim 8, wherein the holder includes a plurality of separate conductive spots, and for each conductive spot, a hydrophilic zone surrounds the conductive spot, and, for each conductive spot, a hydrophobic zone surrounds the hydrophilic zone.

10. A droplet holder as recited in claim 8, wherein the holder is adapted for use in a measuring instrument utilizing surface plasmon resonance to analyze the analyte in the droplet; and wherein the conductive spot has a first surface that is in contact with the top surface of the slide, and a second surface opposite to the first surface; and wherein the droplet covers the entire surface area of the second surface of the conductive spot.

11. A droplet holder as recited in claim 8, wherein the hydrophilic zone captures the periphery of the droplet to keep the periphery of the droplet and the increased concentration of the analyte therein away from the conductive spot, leaving the relatively uniform concentration of the analyte in the central part of the droplet, the central part overlying the conductive spot, to reduce the measurement distortion result of the droplet "peripheral concentration effect";

and wherein the hydrophobic zone restricts the periphery of the droplet to the hydrophilic zone.

12. A droplet holder as recited in claim 1, wherein the surface of the spot that is not in contact with the top surface of the slide comprises gold or silver.

13. A droplet holder as recited in claim 4, wherein the surface of the spot that is not in contact with the top surface of the slide comprises gold or silver.

14. A droplet holder as recited in claim 8 wherein the surface of the spot that is not in contact with the top surface of the slide comprises gold or silver.

\* \* \* \* \*